United States Patent [19]

Perronnet et al.

[11] 4,020,076
[45] Apr. 26, 1977

[54] NOVEL PHOSPHORYLOXY-THIAZOLES

[75] Inventors: Jacques Perronnet, Paris; Laurent Taliani, Les Pavillons-sous-Bois, both of France

[73] Assignee: Roussel-UCLAF, Paris, France

[22] Filed: Sept. 9, 1975

[21] Appl. No.: 611,710

[30] Foreign Application Priority Data

Sept. 20, 1974 France .................. 74.31841

[52] U.S. Cl. ............... 260/302 E; 260/302 R; 260/306.7 R; 260/455 A; 424/200
[51] Int. Cl.² .................. C07D 277/56
[58] Field of Search .................. 260/302 E

[56] References Cited

UNITED STATES PATENTS

| | | | |
|---|---|---|---|
| 3,518,279 | 6/1970 | Miller | 260/302 E |
| 3,758,487 | 9/1973 | Hoffman | 260/302 E |
| 3,784,554 | 1/1974 | Barker | 260/302 E |
| 3,856,897 | 12/1974 | Fan | 260/302 E |

*Primary Examiner*—R. J. Gallagher
*Attorney, Agent, or Firm*—Hammond & Littell

[57] ABSTRACT

Novel 4-phosphoryloxy-5-cyano-thiazoles of the formula

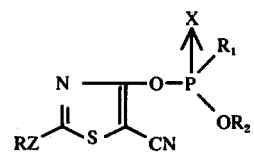

wherein R is selected from the group consisting of alkyl of 1 to 6 carbon atoms, alkenyl of 2 to 6 carbon atoms, cycloalkyl of 3 to 8 carbon atoms and benzyl optionally substituted with 1 to 2 members of the group consisting of halogen, methyl and methoxy, $R_1$ is selected from the group consisting of alkyl and alkoxy of 1 to 3 carbon atoms, $R_2$ is alkyl of 1 to 3 carbon atoms and X and Z are individually selected from the group consisting of oxygen and sulfur having particularly insecticidal properties but also acaricidal and nematocidal properties.

18 Claims, No Drawings

NOVEL PHOSPHORYLOXY-THIAZOLES

OBJECTS OF THE INVENTION

It is an object of the invention to provide the novel 4-phosphoryloxy-5-cyano-thiazoles of formula I and novel intermediates therefore.

It is another object of the invention to provide a novel process for the preparation of the thiazoles formula I.

It is a further object of the invention to provide novel pesticidal compositions and to a novel method of killing pests, particularly insects.

These and other objects and advantages of the invention will become obvious from the following detailed description.

THE INVENTION

The novel 4-phosphoryloxy-5-cyano-thiazoles of the invention have the formula

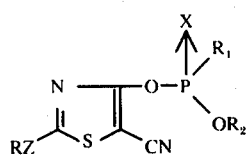

wherein R is selected from the group consisting of alkyl of 1 to 6 carbon atoms, alkenyl of 2 to 6 carbon atoms, cycloalkyl of 3 to 8 carbon atoms and benzyl optionally substituted with 1 to 2 members of the group consisting of halogen, methyl and methoxy, $R_1$ is selected from the group consisting of alkyl and alkoxy of 1 to 3 carbon atoms, $R_2$ is alkyl of 1 to 3 carbon atoms and X and Z are individually selected from the group consisting of oxygen and sulfur.

Among the preferred compounds of formula I, $R_1$ is preferably methyl, ethyl, propyl, methoxy, ethoxy, or propoxy, $R_2$ is preferably methyl, ethyl or propyl and R is preferably methyl, ethyl, propyl, butyl, pentyl, hexyl, cyclopropyl, cyclobutyl, cyclopentyl, cyclohexyl, benzyl, p-chlorobenzyl or p-methylbenzyl. R is preferably alkyl of 1 to 6 carbon atoms.

The novel process of the invention for the preparation of compounds of formula I comprises reacting a compound of the formula

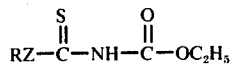

wherein R and Z have the above definitions with chloroacetonitrile in the presence of a base to obtain a thiazole of the formula

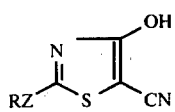

and reacting the latter with a phosphate derivative of the formula

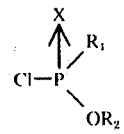

wherein X, $R_1$ and $R_2$ have the above definitions to obtain the corresponding compound of formula I.

The compounds of formula II wherein Z is sulfur may be prepared, as a part of the invention by reacting a mercaptan of the formula RSH with an ethoxy carbonyl isothiocyanate. The compounds of formula II wherein X is oxygen may be prepared in an analogous manner.

The compounds of formula I may be prepared from the sodium or potassium salt of N-carbethoxy-thiocarbamate of formula II. The base present in the reaction with chloroacetonitrile is preferably an alkali metal alcoholate such as potassium methylate or sodium ethylate but organic bases such as pyridine or triethylamine may also be used. The base used for this reaction is employed at the rate of 2 equivalents in the case of the compound of formula II or one equivalent when the alkali metal salt is reacted, to effect the cyclization. The reaction is effected preferably in an organic solvent such as alcohol, acetonitrile, benzene or toluene.

The novel intermediate products of the invention are the 4-hydroxy-5-cyano-thiazoles of formula III and the N-carbethoxy-thiocarbamates of formula II wherein Z is sulfur. The following compounds of formula II wherein Z is oxygen are also novel: cyclohexyl N-carbethoxy-thiocarbamate, p-chlorobenzyl N-carbethoxy-thiocarbamate, benzyl N-carbethoxy-thiocarbamate and p-methyl-benzyl N-carbethoxy-thiocarbamate, the n-butyl N-carbethoxy-thiocarbamate and its potassium salt.

The novel pesticidal compositions of the invention are comprised of an effective amount of at least one compound of formula I and a carrier. The compositions preferably contain 10 to 80% by weight of the compounds of formula I.

The compositions may be in the form of powders, granules suspensions, emulsions or solutions containing besides the active principle cationic, anionic or nonionic surface active agents, inert powders such as talc, clay, silicates or kieselguhr and a vehicle such as water, alcohol, hydrocarbons of other organic solvents or a mineral, animal or vegetable oil.

The compositions are useful for killing pests such as insects, acaricides or nematodes and are useful in agriculture to combat these pests, particularly insects.

The novel method of the invention for killing pests comprises contacting the pests with a lethal amount of at least one compound of formula I.

In the following examples there are described several preferred embodiments to illustrate the invention. However, it should be understood that the invention is not intended to be limited to the specific embodiments.

EXAMPLE 1

5-cyano-4-diethoxyphosphoryloxy-2-ethoxy-thiazole

STEP A: 5-cyano-4-hydroxy-2-ethoxy-thiazole 22.8 g of chloroacetonitrile were added dropwise with stirring at room temperature to a suspension of 61.5 g of the potassium salt of ethyl N-carbethoxy-thiocarbamate [described by Guha et al, Indian Chem.

Soc., Vol. 6 (1929), p. 570] in one liter of methanol and after stirring the mixture for 2 hours, 30 g of triethylamine were added thereto. The mixture was stirred for another 48 hours and was then refluxed for 2 hours and filtered. The filtrate was concentrated to dryness and the residue was added to sodium hydroxide solution. The resulting solution was washed with ethyl ether, acidified with hydrochloric acid and extracted with ethyl ether. The extracts were dried and evaporated to dryness and the residue was crystallized from petroleum ether to obtain 26.4 g of 5-cyano-4-hydroxy-2-ethoxy-thiazole melting at 132°C.

STEP B:

5-cyano-4-diethoxyphosphoryloxy-2-ethoxy-thiazole 5.5 of triethylamine and 7.2 g of 0,0-diethyl chlorophosphate were added to a suspension of 8.5 g of 5-cyano-4-hydroxy-2-ethoxy-thiazole in 200 ml of acetonitrile and the reaction mixture was then stirred for 24 hours at room temperature. The mixture was concentrated to dryness and the residue was taken up in ethyl ether. The ether phase was washed with water, then sodium solution, was dried and concentrated to dryness to obtain 4.3 g of 5-cyano-4-diethoxyphosphoryloxy-2-ethoxy-thiazole in the form of a yellow oil with a refractive index of $n_D^{22} = 1.4928$.

Analysis: $C_{10}H_{15}N_2O_5PS$: Calculated: %C 39.21; %H 4.94; %N 9.14; %P 10.11. Found: C 39.2; H 5.2; N 8.7; 10.2.

EXAMPLE 2

5-cyano-4-diethoxythiophosphoryloxy-2-ethoxy-thiazole 18.9 g of 0,0-diethyl chlorothiophosphate were added to a suspension of 17 g of 5-cyano-4-hydroxy-2-ethyoxythiazole, 10 g of triethylamine and 100 ml of acetonitrile and the reaction mixture was stirred for 24 hours and then was poured into water. The mixture was decanted and the aqueous phase was extracted with benzene, was dried and evaporated to dryness. The oil residue was chromatographed over silica gel and was eluted with a 6-4 cyclohexane-ethyl acetate mixture to obtain 24.5 g of 5-cyano-4-diethoxythiophosphoryloxy-2-ethoxy-thiazole in the form of a yellow oil with a refractive index $n_D^{22} = 1.5182$.

Analysis: $C_{10}H_{15}N_2O_4PS_2$: Calculated: %C 37.26; %H 4.69; %N 8.69; %P 9.61; Found: C 37.6; H 4.8; N 8.4; P 9.6.

EXAMPLE 3

5-cyano-4-dimethoxythiophosphoryloxy-2-ethoxy-thiazole

First 22 g of potassium carbonate and then 25.6 g of 0,0-dimethyl chlorothiophosphate were added to 27.2 g of 5-cyano-4-hydroxy-2-ethoxy-thiazole in 300 ml of acetone and the reaction mixture was stirred for 24 hours at room temperature and then was filtered. The filtrate was evaporated to dryness to obtain a brown oil which was chromatographed over silica gel. Elution was with a 1-1 cyclohexane-ethylacetate mixture and the product was crystallized from petroleum ether to obtain 6.6 g of 5-cyano-4-dimethoxythiophosphoryloxy-2-ethoxy-thiazole in the form of beige crystal melting at 48° C.

Analysis: $C_8H_{11}N_2O_4PS_2$: Calculated: %C 32.65; %H 3.77; %N 9.52; %P 10.54. Found: C 33.0; H 3.8; N 9.4; P 10.5.

EXAMPLE 4

2-n-butoxy-4-dimethoxythiophosphoryloxy-5-cyano-thiazole

STEP A: 2-n-butoxy-4-hydroxy-5-cyano-thiazole 26 g of ethoxycarbonyl isothiocyanate were added dropwise to a mixture of 0.4 ml of triethylamine, 15 g of normal butanol and 150 ml of tetrahydrofuran and the mixture was refluxed for 2 hours and concentrated to dryness by distillation under reduced pressure to obtain 39 g of raw n-butyl N-carbethoxy-thiocarbamate. The latter product was added to a mixture of 500 ml of methanol and 14 g of potassium methylate and the mixture was stirred for an hour and then concentrated to dryness under reduced pressure. The residue was added to ether and the precipitate formed was recovered by vacuum filtration and was dried to obtain 35 g of the potassium salt of n-butyl N-carbethoxy-thiocarbamate melting at 219° C.

Analysis: $C_8H_{14}KNO_3S$: Calculated: %C 39.48; %H 5.8; %N 5.75; %S 13.18. Found: C 39.2; H 5.8; N 5.8; S 12.8.

A mixture of 35 g of the potassium salt of n-butyl N-carbethoxy-thiocarbamate, 500 ml of methanol and 7.7 ml of chloroacetonitrile was stirred for 5 hours and then 10.1 g of potassium methylate were added thereto. The reaction mixture was refluxed for 16 hours and was then evaporated to dryness. The residue was dissolved in water and the aqueous phase was washed with ether and then acidified. The acid aqueous phase was extracted with ether and the ether phase was evaporated to dryness to obtain 16 g of 2-n-butoxy-4-hydroxy-5-cyano-thiazole in the form of beige crystals melting at 80° C.

Analysis: $C_8H_{10}N_2O_2S$: Calculated: %C 48.47; %H 5.08; %N 14.13; %S 16.17. Found: C 48.7; H 5.2; N 14.0; S 16.3.

STEP B:

2-n-butoxy-4-dimethoxythiophosphoryloxy-5-cyano-thiazole 6.3 ml of 0,0-dimethyl chlorophosphate were added to a suspension of 10 g of 2-n-butoxy-4-hydroxy-5-cyano-thiazole and 7 g of potassium carbonate in 70 ml of acetonitrile and the reaction mixture was stirred at room temperature for 16 hours and was then filtered. The filtrate was evaporated to dryness and the residue was chromatographed over silica gel. Elution with a 1-1 cyclohexane-ethyl acetate mixture resulted in 8.5 g of 2-n-butoxy-4-dimethoxythiophosphoryloxy-5-cyano-thiazole in the form of an oil with a refractive index $n_D^{25} = 1.5241$.

Analysis: $C_{10}H_{15}N_2O_4PS_2$: Calculated: %C 37.26; %H 4.69; %N 8.69; %P 9.61. Found: C 37.5; H 4.9; N 8.5; P 9.4.

EXAMPLE 5

2-n-butoxy-4-diethoxythiophosphoryloxy-5-cyano-thiazole

Using the procedure of Step B of Example 4, 1 g of 2-n-butoxy-4-hydroxy-5-cyano-thiazole was reacted with 0.8 ml of 0,0-diethyl chlorothiophosphate to obtain 1 g of 2-n-butoxy -4-diethoxythiophosphoryloxy-5-cyano-thiazole in the form of an oil with a refractive index $n_D^{22} = 1.5094$.

EXAMPLE 6
2-cyclohexyloxy-4-diethoxythiophosphoryloxy-5-cyano-thiazole

STEP A: cyclohexyl N-carbethoxy-thiocarbamate 65.6 g of ethoxycarbonyl isothiocyanate were added to a mixture of 50.1 g of cyclohexanol, 100 ml of tetrahydrofuran and 10 ml of triethylamine and the mixture was refluxed for 20 hours after which the tetrahydrofuran was distilled under reduced pressure. Ether was added to the residue and the ether phase was extracted with aqueous potassium hydroxide solutions. The aqueous phase was recovered by decanting and was acidified with N hydrochloric acid. The aqueous phase was extracted with ether and the ether phase was dried and concentrated to dryness under reduced pressure to obtain 82 g of cyclohexyl N-carbethoxy-thiocarbamate. The product was purified by chromatography over silica gel with elution with an 8-2 cyclohexane-ethyl acetate mixture.

STEP B: 2-cyclohexyloxy-4-hydroxy-5-cyano-thiazole

A suspension of 38.3 g of cyclohexyl N-carbethoxy-thiocarbamate and 11.56 g of potassium ethylate in 400 ml of methanol was stirred for 2 hours and 12.45 g of chloroacetonitrile were added thereto. The mixture was stirred for 48 hours at room temperature and was then concentrated to dryness. The residue was added to water and the aqueous phase was acidified with hydrochloric acid. The aqueous phase was extracted with ether and the ether phase was dried and concentrated to dryness to obtain 15 g of 2-cyclohexyloxy-4-hydroxy-5-cyanothiazole in the form of white crystals melting at 138° C. Analysis: $C_{10}H_{12}N_2O_2S$: Calculated: %C 53.56; %H 5.40; %N 12.50; %S 14.30. Found: C 53.7; H 5.5; N 12.2; S 14.6.

STEP C: 2-cyclohexyloxy-4-diethoxythiophosphoryloxy-5-cyano-thiazole

A mixture of 12.44 g of diethyl chlorothiophosphate, 6.67 g of triethylamine and 15 g of 2-cyclohexyloxy-4-hydroxy-5-cyano-thiazole was stirred for 3 days and then concentrated to dryness. The residue was added to water and the aqueous phase was extracted with ether. The ether phase was dried and evaporated to dryness. The residue was crystallized from pentane and then isopropyl ether to obtain 10 g of 2-cyclohexyloxy-4-diethoxythiophosphoryloxy-5-cyano-thiazole in the form of white crystals melting at 58° C.

EXAMPLE 7
2-p-chlorobenzyloxy-4-diethoxythiophosphoryloxy-5-cyano-thiazole

STEP A: p-chlorobenzyl N-carbethoxythiocarbamate 90 g of ethoxycarbonyl isothiocyanate were added dropwise to a mixture of 85 g of p-chlorobenzyl alcohol, 600 ml of tetrahydrofuran and 4 ml of triethylamine and the mixture was refluxed for 24 hours and was then evaporated to dryness under reduced pressure. The residue was added to isopropyl alcohol and the precipitate formed was recovered by vacuum filtration to obtain 95 g of p-chlorobenzyl N-carbethoxy-thiocarbamate melting at 95° C.

Analysis: $C_{11}H_{12}ClNO_3S$: Calculated: %C 48.27; %H 4.42; %Cl 11.71; %N 5.12; %S 11.71. Found: C 48.3; H 4.7; Cl 11.7; N 5.1; S 12.0.

STEP B: Sodium salt of 2-p-chlorobenzyloxy-4-hydroxy-5-cyano-thiazole

A suspension of 54.6 g of p-chlorobenzyl N-carbethoxy-thiocarbamate, 11.2 g of sodium methylate and 300 ml of ethanol was stirred for 30 minutes and 15 g of chloroacetonitrile were then added thereto. The mixture was refluxed for 30 minutes, then cooled and 11.2 g of sodium methylate were added. The mixture was stirred at room temperature for 24 hours and was then concentrated to dryness. The residue was taken up in water and the aqueous phase was filtered to obtain 24 g of sodium salt of 2-p-chlorobenzyloxy-4-hydroxy-5-cyano-thiazole melting at 200° C.

STEP C: 2-p-chlorobenzyloxy-4-diethoxythiophosphoryloxy-5-cyano-thiazole 9.5g of 0,0-diethyl chlorothiophosphate were added to a suspension of 14.4 g of sodium salt of 2-p-chlorobenzyloxy-4-hydroxy-5-cyano-thiazole in 200 ml of acetone and the reaction mixture was stirred for 24 hours at room temperature. The mixture was filtered and the filtrate was evaporated to dryness. The residue was chromatographed over silica gel and was eluted with an 8-2 cyclohexane-ethyl acetate mixture to obtain 4.2 g of 2-p-chlorobenzyloxy-4-diethoxythiophosphoryloxy-5-cyano-thiazole in the form of white crystals melting at 66° C.

Analysis: $C_{15}H_{16}ClN_2O_4PS_2$: Calculated %C 43.02; %H 3.86; %Cl 8.46; %N 6.70; %P 7.41. Found: C 43.2; H 3.8; Cl 8.8; N 6.6; P 7.1.

EXAMPLE 8
2-p-chlorobenzyloxy-4-dimethoxythiophosphoryloxy-5-cyano-thiazole

Using the procedure of Step B of Example 7, 10 g of sodium 2-p-chlorobenzyloxy-4-hydroxy-5-cyano-thiazole were reacted with 5.6 g of 0,0-dimethyl chlorothiophosphate to obtain 4.2 g of 2-p-chlorobenzyloxy-4-dimethoxythiophosphoryloxy-5-cyano-thiazole in the form of white crystals melting at 49° C.

Analysis: $C_{13}H_{12}ClN_2O_4PS_2$: Calculated: %C 39.96; %H 3.10; %Cl 9.08; %N 7.17; %P 7.92. Found: C 40.5; H 3.1; Cl 9.5; N 7.1; P 7.8.

EXAMPLE 9
2-ethylthio-4-diethoxythiophosphoryloxy-5-cyano-thiazole

STEP A: ethyl N-carbethoxy-dithiocarbamate 66 g of ethoxycarbonyl isocyanate were added dropwise to a mixture of 500 ml of petroleum ether (b.p. = 65–75° C), 62 g of ethyl mercaptan and 1 ml of triethylamine and after cooling the mixture to −10° C, the mixture was vacuum filtered. The precipitate was washed with petroleum (b.p. = 65–75° C) and was dried to obtain 92 g of ethyl N-carbethoxy-dithiocarbamate melting at 60° C. For anaylsis, the product was crystallized from a 1-1petroleum ether (b.p. = 65–75° C)-isopropyl ether to obtain a microanalytically pure product melting at 60° C.

Analysis: $C_6H_{11}NO_2S_2$: Calculated: %C 37.29; %H 5.73; %N 7.25; %S 33.18. Found: C 37.4; H 5.8; N 7.2; S 33.5.

STEP B: 2-ethylthio-4-hydroxy-5-cyano-thiazole

A suspension of 40 g of ethyl N-carbethoxy-dithiocarbamate, 14 g of potassium methylate, 15 g of chloroacetonitrile and 1 g of potassium iodide in 250 ml of methanol was stirred for 3 hours at room temperature under an inert atmosphere and then 14 g of potassium methylate were added. The reaction mixture was refluxed for one hour and water was then added thereto. The aqueous phase was washed with ethyl acetate and then acidified with concentrated hydrochloric acid. The aqueous phase was extracted with ethyl acetate and the extracts were dried, filtered and evaporated to dryness. The residue was empasted with isopropyl ether and then filtered to obtain 14 g of 2-ethylthio-4-hydroxy-5-cyano-thiazole in the form of cream crystals melting at 160° C.

Analysis: $C_6H_6N_2OS_2$: Calculated: %C 38.70; %H 3.25; %N 15.05; %S 34.4. Found: C 38.7; H 3.2; N 14.7; S 34.3.

STEP C:
2-ethylthio-4-diethoxythiophosphoryloxy-5-cyano-thiazole

A suspension of 7.6 g of 2-ethylthio-4-hydroxy-5-cyano-thiazole, 5.6 g of potassium carbonate, 7.6 g of 0,0-diethyl chlorothiophosphate and 100 ml of acetone was stirred for 12 hours at room temperature and then was filtered. The filtrate was evaporated to dryness and the residue was chromatographed over silica gel. Elution with 9-1 cyclohexaneethyl acetate yielded 8.5 g of 2-ethylthio-4-diethoxythiophosphoryloxy-5-cyano-thiazole in the form of an oil with a refractive index $n_D^{20} = 1.5655$.

Analysis: $C_{10}H_{15}N_2O_3PS_3$: Calculated: %C 35.50; %H 4.47; %N 8.28; %P 9.15. Found: C 35.7; H 4.5; N 8.2; P 9.0.

EXAMPLE 10
2-ethylthio-4-dimethoxythiophosphoryloxy-5-cyano-thiazole

Using the procedure of Step B of Example 9, 4.8 g of 2-ethylthio-4-hydroxy-5-cyano-thiazole and 3.8 g of 0,0-dimethyl chlorothiophosphate were reacted to obtain 5 g of 2-ethylthio-4-dimethoxythiophosphoryloxy-5-cyano-thiazole in the form of an oil with a refractive index $n_D^{20} = 1.584$.

Analysis: $C_8H_{11}N_2O_3PS_3$: Calculated: %C 31.95; %H 3.58; %N 9.03; %P 9.98. Found: C 32.1; H 3.6; N 9.0; P 9.6.

EXAMPLE 11
2-benzyloxy-4-diethoxythiophosphoryloxy-5-cyano-thiazole

STEP A: Sodium salt of 2-benzyloxy-4-hydroxy-5-cyano-thiazole

A mixture of 162 g of benzyl alcohol and 196 g of ethoxycarbonyl isothiocyanate and 1 ml of triethylamine in 1 liter of tetrahydrofuran was refluxed for 24 hours and was concentrated to dryness. The residue was washed with petroleum ether and isopropyl ether to obtain 256 g of benzyl N-carbethoxy-thiocarbamate melting at 96° C.

A mixture of 47.8 g of benzyl N-carbethoxythiocarbamate, 300 ml of methanol, 10 g of sodium methylate and 15 g of chloroacetonitrile was refluxed for one hour and after the addition of another 10 g of sodium methylate, the mixture was stirred at room temperature for 24 hours. The mixture was evaporated to dryness and the residue was added to water. The aqueous mixture was vacuum filtered to obtain 21.2 g of sodium salt of 2-benzyloxy-4-hydroxy-5-cyano-thiazole.

STEP B:
2-benzyloxy-4-diethoxythiophosphoryloxy-5-cyano-thiazole

A mixture of 12.7 g of the product of Step A and 10.4 g of 0,0-diethyl chlorothiophosphate in 200 ml of acetone was stirred at room temperature for 24 hours and the mixture was evaporated to dryness. The residue was chromatographed over silica gel and was eluted with benzene to obtain 6.2 g of 2-benzyloxy-4-diethoxythiophosphoryloxy-5-cyano-thiazole as an oil with a refractive index $n_D^{21} = 1.5596$.

Analysis: $C_{15}H_{17}N_2O_4PS_2$: Calculated: %C 46.86; %H 4.46; %N 7.28; %P 8.06. Found: C 47.3; H 4.5; N 7.2; P 7.8.

EXAMPLE 12
2-benzyloxy-4-dimethoxythiophosphoryloxy-5-cyano-thiazole

Using the procedure of Step B of Example 11, 9 g of the sodium salt of 2-benzyloxy-4-hydroxy-5-cyano-thiazole and 5.7 g of 0,0-dimethyl chlorothiophosphate was reacted to obtain 4.3 g of 2-benzyloxy-4-dimethoxythiophosphoryloxy-5-cyano-thiazole melting at 47° C.

Analysis: $C_{13}H_{13}N_2O_4PS_2$: Calculated: %C 43.82; %H 3.68; %N 7.86; %P 8.69. Found: C 44.2; H 3.6; N 7.8; P 8.3.

EXAMPLE 13
2-p-chlorobenzylthio-4-diethoxythiophosphoryloxy-5-cyano-thiazole

STEP A:
2-p-chlorobenzylthio-4-hydroxy-5-cyano-thiazole

A mixture of 158.6 g of p-chlorobenzylthio alcohol, 800 ml of tetrahydrofuran, 5 ml of triethylamine and 131.6 g of ethoxycarbonyl isothiocyanate was refluxed for 2½ hours and was then concentrated to dryness. The residue was washed with petroleum ether to obtain 233 g of p-chlorobenzyl N-carbethoxy-dithiocarbamate melting at 80° C.

A mixture of 29 g of p-chlorobenzyl N-carbethoxy-dithiocarbamate, 200 ml of methanol and 5.4 g of sodium methylate was stirred at room temperature for 2 hours and after the addition of 7.4 g of chloroacetonitrile thereto, the mixture was refluxed for an hour. Another 5.4 g of sodium methylate were added and the mixture was refluxed for another hour. After standing at room temperature for 48 hours, the mixture was evaporated to dryness and the residue was washed with water and chloroform. The product was dissolved in hot water which solution was acidified and vacuum filtered. The recovered precipitate was washed with isopropyl ether to obtain 5 g of 2-p-chlorobenzyl-thio-4-hydroxy-5-cyano-thiazole melting at 190° C.

STEP B:
2-p-chlorobenzylthio-4-diethoxythiophosphoryloxy-5-cyano-thiazole

A mixture of 4.5 g of the product of Step A, 75 ml of acetone, 1.78 g of triethylenediamine and 3 g of 0,0-diethyl chlorothiophosphate was stirred for 18 hours and was then filtered. The filtrate was treated with activated carbon and evaporated to dryness. The residue was washed with petroleum ether to obtain 4 g of 2-p-chlorobenzylthio-4-diethoxy-thiophosphoryloxy-5-cyano-thiazole melting at 74° C.

Analysis: $C_{15}H_{16}ClN_2O_3PS_3$: Calculated: %C 41.42; %H 3.70; %Cl 8.15; %N 6.44; %P 7.12. Found: C 41.5; H 3.7; Cl 8.0; N 6.5; P 7.0.

EXAMPLE 14

2-p-chlorobenzyloxy-4-ethoxymethylthiophosphonyloxy-5cyanothiazole

A mixture of 10 g of the sodium salt of 2-p-chlorobenzyloxy-4-hydroxy-5-cyano-thiazole, 100 ml of acetone and 5.5 g of 0-ethyl methylthiophosphono chloridate was stirred for 24 hours at room temperature and was filtered. The filtrate was evaporated to dryness and the residue was chromatographed over silica gel. Elution with benzene yielded 4.2 g of 2-p-chlorobenzyloxy-4-ethoxymethylthiophosphonyloxy -5-cyano-thiazole as an oil with a refractive index $n_D^{23}$= 1.5838.

Analysis: $C_{14}H_{14}ClN_2O_3PS_2$:
Calculated: %C 43.25; %H 3.63; %Cl 9.12; %N 7.0.
Found: C 43.5; H 3.7; Cl 9.8; 7.0.

EXAMPLE 15

2-ethoxy-4-dimethoxyphosphoryloxy-5-cyano-thiazole

A mixture of 17 g of 2-ethoxy-4hydroxy-5-cyano-thiazole, 14 g of potassium carbonate, 13 g of O,O-dimethyl chlorophosphate and 150 ml of acetone was stirred for 3 hours at room temperature and the mixture was concentrated to dryness. The residue was added to an aqueous sodium chloride solution which was then extracted with ethyl ether. The ether extracts were washed with an aqueous 2% sodium hydroxide solution, dried and evaporated to dryness to obtain 14.4 g of 2-ethoxy-4-dimethoxyphosphoryloxy-5-cyano-thiazole as an oil with a refractive index $n_D^{23}$ = 1.5056.

Analysis: $C_8H_{11}N_2O_5PS$:
Calculated: %C 34.54; %H 3.99; %N 10.07; %P 11.13.
Found: C 34.7; H4.1; N 9.8; P 10.7.

EXAMPLE 16

2-p-methylbenzyloxy-4-diethoxythiophosphoryloxy-5-cyano-thiazole

STEP A: Sodium salt of 2-p-methylbenzyloxy-4-hydroxy-5-cyano -thiazole 66.5 g of ethoxycarbonyl isothiocyanate were added dropwise to a solution of 61 g of p-methylbenzyl alcohol in 500 ml of tetrahydrofuran and 2 ml of triethylamine and the mixture was refluxed for 24 hours. The mixture was concentrated to dryness to obtain 135 g of raw p-methylbenzyl N-carbethoxy -thiocarbamate.

The 135 g of said product were dissolved in 500 ml of methanol and 29.7 g of sodium methylate were added thereto. The mixture was stirred at room temperature for 10 minutes and after the dropwise addition of 37.5 g of chloroacetonitrile, the mixture was refluxed for one hour. After the addition of another 29.7 g of sodium methylate, the mixture was stirred at room temperature and then evaporated to dryness. The residue was added to water and the precipitate formed was recovered by vacuum filtration and was washed with acetone to obtain 28.2 g of the sodium salt of 2-p-methylbenzyloxy-4-hydroxy-5-cyano-thiazole melting at 220° C with decomposition.

STEP B:
2-p-methylbenzyloxy-4-diethoxythiophosphoryloxy-5-cyano- thiazole

A mixture of 13.4 g of the sodium salt of Step A, 10 g of 0,0-diethyl chlorothiophosphate and 200 ml of acetone was refluxed for 24 hours and was then filtered to remove inorganic salts. The filtrate was evaporated to dryness and the residue was chromatographed over silica gel. Elution with an 8-2 cyclohexane-ethylacetate mixture gave 7 g of 2-p-methylbenzyloxy-4-diethoxythiophosphoryloxy-5-cyano-thiazole melting at 58° C.

Analysis: $C_{16}H_{19}N_2O_4PS_2$:
Calculated: %C 48.23; %H 4.81; %N 7.03; %P 7.77.
Found: C 48.3; H 4.8; N 7.0; P 7.5.

EXAMPLE 17

Compositions consisting of 15% by weight of 2-ethoxy-4-diethoxythiophosphoryloxy-5-cyano-thiazole, 6.4% by weight of Atlox 4851 (oxyethylene triglyceride with a sulfonate having an acid No. of 1.5), 3.2% by weight of Atlox 4855 (oxyethylene triglyceride with a sulfonate having a acid No. of 3) and 75.4% by weight of xylene are useful as insecticides, acaricides, or nematicides.

EXAMPLE 18

A composition consisting of 15% by weight of 2-ethoxy-4-dimethoxyphosphoryloxy-5-cyano-thiazole, 6.4% by weight of Atlox 4851, 3.2% by weight of Atlox 4855 and 75.4% by weight of xylene is useful as an insecticide.

PESTICIDAL ACTIVITY

The pesticidal activity was determined for 2-ethoxy-4-diethoxythiophosphoryloxy-5-cyano-thiazole (compound A), 2-n-butyoxy-4-dimethoxythiophosphoryloxy-5-cyano-thiazole (compound B), 2-ethoxy-4-dimethoxythiophosphoryloxy-5-cyanothiazole (compound C) and 2-ethoxy-4-dimethoxyphosphoryloxy-5-cyano-thiazole (compound D).

A. Insecticidal Activity a. Activity against *Drosophila melanogaster*

This test measures the vapor activity of the compounds and the less than 48 hours old insects were placed in a Petri dish with a 10 cm diameter connected by a tergal screen to a crystallizer of the same diameter in which the test compound in acetone solution is placed. The said solution is evaporated after the insects have been placed and 3 tests with 25 insects were run for each concentration. The results are expressed in Table I as a percentage of mortality after 1, 2, 4 and 6 hours.

TABLE I

| Compound | Concentration in ppm | 500 | 50 | 5 |
|---|---|---|---|---|
| 1 H | | 100 | 100 | 99 |

TABLE I-continued

| Compound | Concentration in ppm | 500 | 50 | 5 |
|---|---|---|---|---|
| A | 4 H | 100 | 100 | 100 |
|  | 6 H | 100 | 100 | 100 |
|  | 1 H | 100 | 77 | 0 |
| B | 4 H | 100 | 100 | 100 |
|  | 6 H | 100 | 100 | 100 |
|  | 1 H | 100 | 100 | 98 |
| C | 4 H | 100 | 100 | 100 |
|  | 6 H | 100 | 100 | 100 |
|  | 2 H | 100 |  |  |
| D | 6 H | 100 |  |  | b. Activity against *Blattella germanica*

This test was a topical application in which adult male *Blattella germanica* received 2 microliters of an acetone solution of the test products between the second and third pair of paws. After this treatment, the test insects were held in a dim light at 20° C and were fed. The results expressed as percent of mortality in Table II were read 24 and 48 hours and 5 days after the treatment.

TABLE II

| Compound | Concentration in ppm | 5000 | 1250 | 625 | 312.5 |
|---|---|---|---|---|---|
| A | 24 H |  | 100 | 100 | 65 |
|  | 48 H |  | 100 | 100 | 70 |
|  | 5 Days |  | 100 | 30 |  |
| C | 24 H |  | 100 | 100 | 80 |
|  | 48 H |  | 100 | 100 | 80 |
|  | 5 Days |  | 100 | 100 | 80 |
| D | 24 H | 100 |  |  |  |
|  | 48 H | 100 |  |  |  |
|  | 5 Days | 100 |  |  |  | c. Test against *Sitophilus granarius*

This topical application test comprised preparing the test compounds in acetone solution at concentrations of 5000, 500 and 50 mg of the active compound per liter and 0.2 μl of the solutions were applied to the ventral thorax of 50 *Sitophilus granarius* for each concentration. The number of individuals alive and those dead was determined at different times and the percent mortality is reported in Table III.

TABLE III

| Compound | Concentration in ppm | 5000 | 500 | 50 |
|---|---|---|---|---|
| A | 4 H | 100 | 100 | 0 |
|  | 24 H | 100 | 100 | 0 |
|  | 5 Days | 100 | 100 | 0 |
| B | 4 H | 100 | 96 | 0 |
|  | 24 H | 100 | 100 | 0 |
|  | 5 Days | 100 | 100 | 0 |
| C | 4 H | 100 | 0 | 0 |
|  | 24 H | 100 | 54 | 0 |
|  | 5 Days | 100 | 96 | 0 |
| D | 4 H | 100 |  |  |
|  | 24 H | 100 |  |  |
|  | 5 Days | 100 |  |  | d. Activity against *Musca domestica*

This topical application test consisted of placing a microliter of an acetone solution of the test product on the dorsal thorax of *Musca domestica* after having been put to sleep with ether. The insects were held at 20° C and 50% relative humidity and were fed milk and water. The percent of mortality was determined 1 hour and 24 hours after the treatment and the results are reported in Table IV.

TABLE IV

| Compound | Concentration in ppm | 5000 | 2500 | 500 |
|---|---|---|---|---|
| A | 1 H | 100 | 100 | 91 |
|  | 24 H | 100 | 100 | 94 |
| B | 1 H | 100 | 100 | 96 |
|  | 24 H | 100 | 100 | 100 |
| C | 1 H | 100 | 100 | 100 |
|  | 24 H | 100 | 100 | 97 |
| D | 1 H |  |  |  |
|  | 24 H | 64 |  |  | e. Activity against *Spodoptera littoralis*

This test was effected with *Spodoptera littoralis* caterpillars 1 to 1.5 cm long and an average of 10 days old. In this ingestion test, 4 ml of an acetone solution of the test products was placed on lettuce rings with an 8 mm diameter which were placed in closed plastic dishes with a 5 cm diameter. 15 caterpillars were placed in each dish and were held at 20° C and 50% relative humidity and were fed when the insects had eaten the treated lettuce ring. The percent of mortality of 1, 24 and 48 hours after treatment is reported in Table V.

TABLE V

| Compound | Concentration in ppm | 250 | 125 | 62.5 |
|---|---|---|---|---|
| A | 1 H | 0 | 0 | 0 |
|  | 24 H | 90 | 100 | 60 |
|  | 48 H | 100 | 100 | 80 |
|  |  | 500 | 250 | 125 |
| B | 1 H | 0 | 0 | 0 |
|  | 24 H | 100 | 100 | 50 |
|  | 48 H | 100 | 100 | 90 |
| C | 1 H | 0 | 0 | 0 |
|  | 24 H | 100 | 80 | 70 |
|  | 48 H | 100 | 80 | 70 | f. Activity against *Aedes aegypti* larvae

10 *Aedes aegypti* larvae in the IV stage in 49 ml of water were added to 200 ml of water and 1 ml of an acetone solution of the test product was added thereto. The percent of mortality determined after 24 and 48 hours is reported in Table VI.

TABLE VI

| | | | % of mortality after | |
|---|---|---|---|---|
| | mg/l | ppm | 24 H | 48 H |
| Compound C | 25 | $10^{-1}$ | 100 | 100 |
|  | 2.5 | $10^{-2}$ | 0 | 0 |
|  | 0.25 | $10^{-3}$ | 0 | 0 | g. Activity against *Musca domestica* larvae

This contact-ingestion test consisted of placing 2 ml of an acetone solution of different concentrations of the test product on 1 g of bran placed in a watch glass and the solvent was evaporated. The treated bran was placed in a plastic dish and was admixed with 2 ml of milk. 20 3 to 4 day old larvae of *Musca domestica* were added to the bran and were held at 20° C and 30% relative humidity and 3 tests were conducted for each concentration. The percent of mortality after 48 hours and 8 days is reported in Table VII.

TABLE VII

| Compound | Concentration in ppm | 5000 | 500 |
|---|---|---|---|
| A | 48 H | 64 | 37 |
|  | 8 Days | 92 | 63 |
|  | 48 H | 93 | 88 |

TABLE VII-continued

| Compound | Concentration in ppm | 5000 | 500 |
|---|---|---|---|
| B | 8 Days | 98 | 98 |
|   | 48 H | 53 | 43 |
| C | 8 Days | 73 | 63 |
|   | 48 H | | |
| D | 8 Days | 90 | | h. Activity againt *Leptinotarsa Decemlineata*

Eggplant leaves with about 40 cm² of surface area (10 × 4 cm) were cut out of untreated plants and were washed with water and dried before being immersed for 10 seconds in an acetone solution of the test product. After drying, the leaves were placed in a plastic ventilated dish and 10 larvae of *Leptinotarsa Decemlineata* in the fourth stage were placed thereon. The percent of mortality after 1, 24 and 48 hours is reported in Table VIII.

TABLE VIII

| | Dose in g/hl | % of mortality after | | |
|---|---|---|---|---|
| | | 1 H | 24 H | 48 H |
| | 100 | 0 | 100 | 100 |
| Compound C | 50 | 0 | 40 | 40 | i. Activity against *Agrostis Segetum* caterpillars

Larvae of *Agrostis Segetum* in the fifth stage were placed in small boxes whose bottom (26 cm on a side) is in the form of a square with a height of 20 cm. The boxes were filled with dirt to a height of 8 cm and 5 lettuce plants of about 15 cm high were planted and 10 caterpillars were placed in each box and after 3 hours, the boxes were each sprayed with 5 ml of an aqueous solution of the test product and the percent of efficacy is reported in Table IX.

TABLE IX

| | Doses in g/hl | % efficacy after | | |
|---|---|---|---|---|
| | | 3 days | 5 days | 7 days |
| | 150 | 80 | 100 | 100 |
| Compound C | 100 | 25 | 50 | 100 |
| | 50 | 50 | 100 | 100 |

2. Acaricide Activity

In an apparatus containing 10 ml of an aqueous solution of the test product, 0.5 ml of water containing about 2000 acariens of *Ditylenchus Myceliophagus* were added thereto and the percent of mortality was determined by a binocular magnifying glass after 24 hours. The test was repeated 3 times corresponding to a sample of 1 ml of test solution and the results are reported in Table X.

TABLE X

| Compound | Concentration in g/l | 0.1 | 0.010 | 0.001 |
|---|---|---|---|---|
| A | Percent of mortality after 24 hours | 100 | 91.6 | 81.8 |
| B | Percent of mortality after 24 hours | 98.5 | 95.9 | 43.3 |
| C | Percent of mortality after 24 hours | 66.84 | | |

3. Nematocidal Activity a. Activity against *Meloidogynes spec*

A volume of about 3 liters of dirt infested with *Meloidogynes spec* was placed in a plastic sack. Nematocidal treatments are considered effective to a depth of 30 cm, a volume of 3 liters of dirt corresponding to a surface area of 100 cm² or $10^{-6}$ ha (since 100 cm² × 30 cm = 3000 ml or 3 liters). Each volume of infested dirt received 100 ml of an aqueous suspension containing 0.250 g of the test product (corresponding to 250 Kg/ha) and the controls received only 100 ml of water. The plastic sacks containing the dirt were immediately sealed after the treatment and then agitated to obtain a good distribution of the product. Two weeks after the treatment, the sacks were opened and the dirt was used to plant 3 tomato plants of St. Pierre variety. The plants used were raised in the greenhouse with dirt sterilized with heat to obtain plants free of nematodes. Three plants were used for each test which was run 6 times for each treatment. Two months after planting the tomatoes were removed from the dirt and the efficacy was determined by counting the number of galls observed on the roots. A correlation between the population of Meloidogynes in the pot and the number of galls exists. The results are reported in Table XI.

TABLE XI

| | Compound C at 250 Kg/ha | Compound D at 25 Kg/ha | Control |
|---|---|---|---|
| Total number of galls | 295 | 125 | 222 |
| Number of galls per foot | 32.77 | 31.25 | 44.4 |
| Relative efficacity in % as compound to controls | 67.4% | 52.8% | — | b. Activity against *Panagrellus silusiae*

30 nematodes were placed on a watch glass and three tests were run for each concentration. The 3 watch glasses for each treatment were placed in a Petri dish with a 15 cm diameter containing a film of water in a manner to retard evaporation of the solution to wet the nematodes. The concentration of the product was 125 mg of MA/L and 1 ml of toxic solution was placed on each watch glass containing the nematodes in 0.5 ml of water. The percent of mortality was determined by a binocular magnifying glass after 24 hours and the results are reported in Table XII.

TABLE XII

| | Dose in g/l | % of mortality |
|---|---|---|
| | 0.1 | 100 |
| Compound B | 0.01 | 100 |
| | 0.001 | 89.3 |

Various modifications of the products and methods of the invention may be made without departing from the spirit or scope thereof and it should be understood that the invention is intended to be limited only as defined in the appended claims.

We claim:
1. A compound of the formula

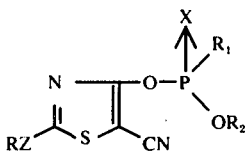

wherein R is selected from the group consisting of alkyl of 1 to 6 carbon atoms, alkenyl of 2 to 6 carbon atoms, cycloalkyl of 3 to 8 carbon atoms and benzyl optionally substituted with 1 to 2 members of the group consisting of halogen, methyl and methoxy, $R_1$ is selected from the group consisting of alkyl and alkoxy of 1 to 3 carbon atoms, $R_2$ is alkyl of 1 to 3 carbon atoms and X and Z are individually selected from the group consisting of oxygen and sulfur.

2. A compound of claim 1 wherein R is alkyl of 1 to 6 carbon atoms.

3. A compound of claim 1 which is 2-ethoxy-4-dimethoxythiophosphoryloxy- 5-cyano-thiazole.

4. A compound of claim 1 which is 2-n-butoxy-4-dimethoxythiophophoryloxy- 5-cyano-thiazole.

5. A compound of claim 1 which is 2-ethoxy-4-diethoxythiophosphoryloxy-5-cyano-thiazole.

6. A compound of claim 1 which is 2-p-chlorobenzyloxy -4-dimethoxythiophosphoryloxy-5-cyano-thiazole.

7. A compound of claim 1 which is 2-n-butoxy-4-diethoxythiophosphoryloxy-5-cyano-thiazole.

8. A compound of claim 1 which is 2-cyclohexyloxy-4-diethoxythiophosphoryloxy-5-cyano-thiazole.

9. A compound of claim 1 which is 2-p-chlorobenzyloxy-4-diethoxythiophosphoryloxy-5-cyano-thiazole.

10. A compound of claim 1 which is 2etylthio-4-diethoxythiophosphoryloxy-5-cyano-thiazole.

11. A compound of claim 1 which is 2-ethylthio-4-dimethoxythiophosphoryloxy-5-cyano-thiazole.

12. A compound of claim 1 which is 2-benzyloxy-4-diethoxythiophosphoryloxy-5-cyano-thiazole.

13. A compound of claim 1 which is 2-benzyloxy-4-dimethoxythiophosphoryloxy-5-cyano-thiazole.

14. A compound of claim 1 which is 2-p-chlorobenzylthio-4-diethoxythiophosphoryloxy-5-cyano-thiazole.

15. A compound of claim 1 which is 2-p-chlorobenzyloxy-4-ethoxymethylthiophosphonyloxy-5-cyano-thiazole.

16. A compound of claim 1 which is 2-p-methylbenzyloxy-4-diethoxythiophosphoryloxy-5-cyano-thiazole.

17. A compound of claim 1 which is 2-ethoxy-4-dimethoxyphosphoryloxy-5-cyano-thiazole.

18. A compound of claim 1 which is 2-ethoxy-4-diethoxyphosphoryloxy-5-cyano-thiazole.

* * * * *